United States Patent [19]

Häberlein et al.

[11] 4,146,530

[45] Mar. 27, 1979

[54] DICYCLOPHOSPHITES AND ORGANIC POLYMERS STABILIZED WITH SAID PHOSPHITES AND THEIR USE AS STABILIZERS

[75] Inventors: Harald Häberlein; Franz Scheidl, both of Gersthofen, Fed. Rep. of Germany

[73] Assignee: Hoechst Aktiengesellschaft, Frankfurt am Main, Fed. Rep. of Germany

[21] Appl. No.: 812,673

[22] Filed: Jul. 5, 1977

[30] Foreign Application Priority Data

Jul. 6, 1976 [DE] Fed. Rep. of Germany ....... 2630257

[51] Int. Cl.² ............................ C07F 9/15; C08K 5/52
[52] U.S. Cl. .......................... 260/45.8 R; 260/348.42; 260/403; 260/927 R
[58] Field of Search ....................... 260/927 R, 45.8 R

[56] References Cited

U.S. PATENT DOCUMENTS

| 3,053,878 | 9/1962 | Friedman et al. | 260/927 R |
| 3,205,250 | 9/1965 | Hechenbleikner | 260/927 R |

*Primary Examiner*—Anton H. Sutto
*Attorney, Agent, or Firm*—Connolly and Hutz

[57] ABSTRACT

The present invention is related to novel phosphites, their use as stabilizers for organic polymers, furthermore to stabilizer compositions containing these novel phosphites as well as the organic polymers being stabilized therewith.

The novel phosphites have a good stabilization effect, especially in combination with known stabilizers, and they are substantially stable against hydrolytical influence. Their volatility and tendency to exudation are very weak.

7 Claims, No Drawings

DICYCLOPHOSPHITES AND ORGANIC POLYMERS STABILIZED WITH SAID PHOSPHITES AND THEIR USE AS STABILIZERS

In order to limit as much as possible the detrimental influence of heat and light on synthetic high polymers, stabilizers and stabilizing additives must be added to the polymers to prevent degradation. Synergistic effects may frequently be achieved by combined addition of stabilizers and stabilizing additives. The commonly applied stabilizing additives are, for example epoxy compounds, antioxidants, multivalent alcohols, compounds absorbing ultra-violet radiation, and organic phosphites.

However, the stabilizing additives are very often not entirely satisfactory, some having a number of shortcomings. For example a series of known organic phosphites which are used for stabilizing purposes show insufficient resistance to hydrolysis and a relatively high degree of volatility. Most of the known phosphites are very unsatisfactory with regard to their non toxicological properties which are required of them more and more in recent time.

The object of the present invention was therefore to find stabilizers based on organic phosphites which do not have said disadvantages and which have a highly stabilizing effect.

The present invention provides phosphites of the formula

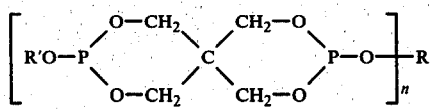

in which n is 1 or 2 and wherein in the case of n being 1,

R and R' are identical or different and at least one of R and R' represents a group of the formula

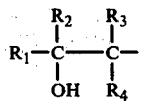

wherein the radicals $R_1$ to $R_4$ stand for identical or different radicals, which may be (a) 0 to 3 hydrogen atoms, (b) a phenyl or naphthyl radical optionally substituted by alkyl groups having of from 1 to 9 carbon atoms, or by 1 to 4 chlorine atoms, or a cycloalkyl radical having of from 5 to 12 carbon atoms, (c) a straight chain or branched alkyl radical having of from 1 to 60 carbon atoms which may be substituted by a phenyl group, an alkylphenyl group having of from 7 to 10 carbon atoms, or a cycloalkyl group having of from 5 to 12 carbon atoms, the radicals indicated sub (b) and (c) may contain further ether, thioether, carboxylic acid ester or epoxide groups, halogen substituents and C=C bonds, and/or $R_2$ and $R_3$ may be common members of a saturated or unsaturated alkylene chain having of from 3 to 10 carbon atoms, and the sum of all carbon atoms contained in the radicals $R_1$ to $R_4$ is at least 4 and not greater than 60, whereas the optionally remaining radical R or R' may be (d) a phenyl or naphthyl radical which may be substituted by alkyl groups having of from 1 to 9 carbon atoms, or by 1 to 4 chlorine atoms, or a cycloalkyl radical having of from 5 to 12 carbon atoms or (e) a straight chain or branched alkyl radical having of from 1 to 60 carbon atoms, which may be substituted by a phenyl group, an alkylphenyl group having of from 7 to 10 carbon atoms, or a cycloalkyl group having of from 5 to 12 carbon atoms, the radicals indicated sub (d) and (e) may further contain ether, thioether, carboxylic acid ester or epoxide groups, halogen substituents and C=C bonds, and the sum of all carbon atoms contained in the radicals R and R' is at least 10, and not greater than 120, and in the case of n being 2, R and R' are different, R' in both parts of the molecule linked by R is equal of different and is defined as in the case of n being 1, and R represents a group of the formula

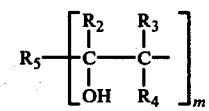

wherein $R_2$, $R_3$ and $R_4$ are defined as in the case of n being 1, $R_5$ represents a bivalent organic radical, and m is 0 or 2, in the case of m being 0 at least one the radicals R' represents a group of the formula

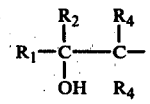

wherein $R_1$ to $R_4$ have the meaning indicated for the case of n being 1 sub (a) to (c) and the optionally remaining radical R' has the meaning indicated for the case of n being 1 sub (d) and (e) and $R_5$ represents a bivalent organic radical, which may be (f) an alkylene chain having of from 2 to 16 carbon atoms and being optionally substituted by methyl or ethyl groups and optionally interrupted by ether, thioether or carboxylic acid ester groups, (g) a phenylene or naphthylene radical which may be substituted by alkyl groups having preferably of from 1 to 9 carbon atoms or by halogen atoms, preferably chlorine or bromine, a m- or p-xylylene radical which may be substituted by 1 to 4 chlorine or bromine atoms, a 1,3- or 1,4-dimethylene cyclohexane radical, a dimethylene tricyclodecane radical, (h) a group of the formula

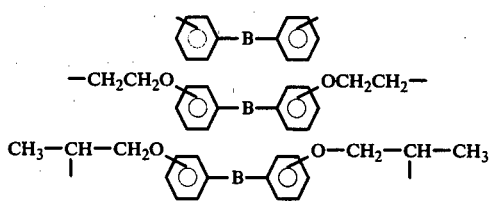

wherein B is —O—, —S—, —CO—, —SO$_2$— or

D and E being equal or different and each represent a hydrogen atom, or an alkyl radical having of from 1 to 6 carbon atoms or D and E may be common members of an alkylene chain having of from 4 to 6 carbon atoms and the sum of all carbon atoms contained in the radicals R and R' is at least 12 and not greater than 120, and in the case of m being 2 the radicals R' in both parts of the molecule linked by R may be identical or different and have the meaning given for n = 1, and $R_5$ represents a bivalent radical, which may be (i) an alkylene chain having of from 1 to 10 carbon atoms and being optionally substituted by methyl or ethyl groups and optionally interrupted by ether, thioether or carboxylic acid ester groups, or (j) a group of the formula $$-CH_2-O-A-O-CH_2-$$

wherein A represents a phenylene or naphthylene radical optionally substituted by alkyl groups having preferably of from 1 to 9 carbon atoms, or by halogen atoms, preferably chlorine or bromine, an alkylene chain optionally having of from 2 to 12 carbon atoms and being substituted by methyl or ethyl groups and optionally interrupted by ether, thioether or carboxylic acid ester groups, a 1,3- or 1,4-dimethylene cyclohexane radical, an α,ω-diacylalkylene radical having of from 3 to 12 carbon atoms, and being optionally substituted by methyl or ethyl groups and optionally interrupted by ether, thioether or carboxylic acid ester groups or C=C bonds, or a diacylphenylene or diacylnaphthylene radical optionally substituted by alkyl groups having preferably of from 1 to 9 carbon atoms, or by halogen atoms, preferably chlorine or bromine, or (k) a group of the formula $$-CH_2-O-\left[\bigcirc-B-\bigcirc\right]-O-CH_2-$$

wherein B has the meaning indicated sub (h) or (l) a group of the formula $$-CH_2-O-CO-\left[\bigcirc-B-\bigcirc\right]-CO-O-CH_2-$$

wherein B has the meaning indicated sub (h), and the sum of all carbon atoms contained in the radicals R and R' is at least 14 and not greater than 120.

It has been found surprisingly that the phosphites according to the invention substantially fulfill the requirements with regard to resistance to hydrolysis, non-toxicological properties and a highly stabilizing effect.

The present invention moreover relates to the use of the hitherto unknown organic phosphites as stabilizers for organic polymers.

A particular advantage of the phosphites according to the invention resides in the fact that they are by far more resistant to hydrolysis than a number of known phosphite stabilizers, and as a consequence thereof, the resistance to weathering of stabilized moulding compositions prepared with their addition is improved.

The use of such phosphites which are present as substances solid at room temperature involves the further advantage that they confer upon plastics articles prepared with their addition a higher dimensional stability under heat than when using known liquid phosphites. Moreover the formation of deposits on the processing machines is highly reduced and the formation of striations on the fabricated shaped articles is considerably reduced. Further valuable properties of the novel phosphites are their inodorousness, their lacking tendency to exudation and their practically lacking volatility.

A number of the phosphites according to the invention is liquid at room temperature, but generally the novel phosphites are solid, white products, a part of which has a wax-like character. The latter which have a flow point/drop-point in the range of from about 35° to 100° C. are of particular interest, as they have not only a stabilizing effect but influence moreover favorably the product properties of the polymer molding compositions wherein they are contained.

The novel phosphites are prepared by transesterifying 2 mols of tri-lower-alkylphosphite or triphenylphosphite with 1 mol of pentaerythritol and by further reacting the primary formed di-lower-alkyl- or diphenyl-pentaerythritol diphosphite with the alcohols R—OH and/or R'—OH, likewise under transesterification conditions.

Solvents, such as toluene, xylene or carbon tetrachloride may be present during the transesterification, but generally do not bring about advantages.

The transesterification reaction can be catalyzed by means of basic substances, such as for example alkali hydroxides, alcoholates and amides, furthermore alkylamines, preferably di- and trialkyl-amines, which are added in an amount of from 0.01 to about 5%, calculated on the weight of the reaction batch.

The transesterification temperature is in the range of from about 60° to 250° C., preferably 180° C. It is generally chosen in a way to assure that the alcohol or phenol set free may be easily distilled off. Alcohol or phenol may be split off more easily by applying a vacuum.

The products of the present invention are obtained as light colored melts, which may be filtered under pressure and which solidify to give wax-like compositions.

In the phosphites of the formula $$\left[\begin{array}{c} R'O-P\begin{array}{c}O-CH_2 \\ O-CH_2\end{array}\begin{array}{c}CH_2-O \\ CH_2-O\end{array}P-O\end{array}\right]_n R$$

n is 1 or 2.

If n is 1, R and R' each represents identical or different radicals, one of which at least is a group of the formula $$R_1-\underset{\underset{OH}{|}}{\overset{\overset{R_2}{|}}{C}}-\underset{\underset{R_4}{|}}{\overset{\overset{R_3}{|}}{C}}-$$

$R_1$, $R_2$, $R_3$ and $R_4$ are identical or different radicals, of which up to three represent hydrogen atoms. The remaining radicals may represent either a phenyl or a naphthyl group, which may be substituted by 1 or 2 alkyl or isoalkyl groups having of from 1 to 9, preferably of from 1 to 4 carbon atoms, or by up to 4 chlorine atoms, for example, phenyl, toluene, xylylene, tertiary butylphenyl, nonylphenyl, chlorophenyl, naphthyl, or chloronaphthyl, or a saturated or unsaturated cycloalkyl radical having of from 5 to 12, preferably of from 5 to 7, carbon atoms, which may be substituted by the aforesaid alkyl groups or by chlorine, for example a cyclophenyl, a cyclohexyl, a cycloheptyl, a cyclooctyl or a cyclododecyl radical.

$R_1$ to $R_4$ finally may preferably represent a straight chain or branched alkyl radical having of from 1 to 60, preferably of from 8 to 40, and especially of from 10 to 30, carbon atoms, which may be substituted by a phenyl group, an alkylphenyl group having of from 7 to 10 carbon atoms or a cycloalkyl group having of from 5 to 12 carbon atoms, for example the ethyl, butyl, hexyl, octyl, decyl, dodecyl, tetradecyl, hexadecyl, octadecyl, eicosyl, docosyl, tetracosyl, hexacosyl, octacosyl, triacontyl, dotriacontyl, tetratriacontyl, hexatriacontyl, octatriacontyl, tetracontyl, or dotetracontyl radical. The radicals $R_1$ to $R_4$ may further contain ether, thioether, carboxylic acid ester or epoxide groups, halogen substituents, preferably chlorine, as well as C=C bonds. The radicals $R_2$ and $R_3$ may further be common members of a saturated or unsaturated alkylene chain having of from 3 to 10, preferably of from 3 to 6, carbon atoms, said chain being optionally substituted by up to 3 alkyl groups having of from 1 to 4 carbon atoms or by an aryl group having of from 6 to 10 carbon atoms. The novel phosphites are moreover characterized by the fact that the total number of all carbon atoms contained in the radicals $R_1$ to $R_4$ is at least 8, and not greater than 60.

If R and R' are different, the remaining radical represents a phenyl or naphthyl group, which may be substituted by 1 to 2 alkyl or isoalkyl groups having of from 1 to 9, preferably of from 1 to 4, carbon atoms or by up to 4 chlorine atoms, for example a phenyl, toluene, xylylene, tertiary butylphenyl, nonylphenyl, chlorophenyl, naphthyl, or chloronaphthyl group, or a saturated or unsaturated cycloalkyl radical having of from 5 to 12, preferably of from 5 to 7, carbon atoms, which may be substituted by the aforesaid alkyl groups or by chlorine. Finally one of the radicals R or R' may represent a straight chain or branched alkyl radical having of from 1 to 60, preferably of from 8 to 40, and especially of from 10 to 30, carbon atoms, which may be substituted by a phenyl group, an alkylphenyl group having of from 7 to 10 carbon atoms or a cycloalkyl group having of from 5 to 12 carbon atoms. The remaining radical R or R' may further contain ether, thioether, carboxylic acid ester or epoxide groups, halogen substituents, preferably chlorine, as well as C=C bonds. If R and R' are different, the sum of all carbon atoms contained therein should be at least 10 and not greater than 120.

If n in the general formula is 2, R and R' are different radicals. R' in both parts of the molecule linked by R may be the same of different and the same meaning as given for n = 1. R represents a group of the formula

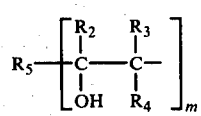

wherein $R_2$, $R_3$ and $R_4$ have the meaning given for n = 1, preferably they represent hydrogen. $R_5$ represents a bivalent organic radical and m is 0 or 2.

If m is 0, at least one of the two radicals R' represents a group of the formula

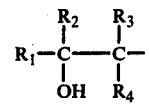

wherein $R_1$, $R_2$, $R_3$ and $R_4$ each has the meaning given of the case of n being 1 and of R being R'; the other radical R' which is optionally different may represent in this case one of the radicals indicated for the case of n being 1 and of R being different from R'.

The bivalent organic radical $R_5$ may represent one of the following groups:

(a) an alkylene chain having of from 2 to 16, preferably of from 2 to 12, carbon atoms, which may be substituted by methyl or ethyl groups and be interrupted by ether, thioether or carboxylic acid ester groups. Examples thereof are ethylene, propylene, 2,2-dimethylpropylene, butylene, pentylene, hexylene, 2-ethylhexylene, octylene, decylene or dodecylene;

(b) a phenylene or naphthylene radical which may be substituted by 1 or 2 alkyl groups having of from 1 to 9 carbon atoms, or by 1 to 4 chlorine or bromine atoms, a m- or p-xylylene radical which may be substituted by 1 to 4 chlorine or bromine atoms, a 1,3- or 1,4-dimethylene cyclohexane radical or a dimethylene tricyclododecane radical;

(c) a group of the formula

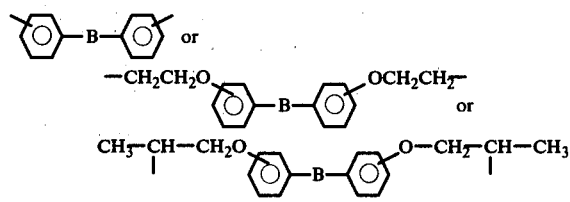

wherein B represents —O—, —S—, —CO—, —SO$_2$— or

D and E being optionally identical or different, and standing for hydrogen atoms or alkyl radicals having of from 1 to 6 carbon atoms or being common members of an alkylene chain having of from 4 to 6 carbon atoms, and the sum of all carbon atoms contained in the radicals R and R' being at least 12, and not greater than 120.

If m is 2, the radicals R' in both parts of the molecule linked by R may be identical or different and have the meaning indicated for the case of n being 1, R being identical with R' and R being different from R'; in this case $R_5$ represents a bivalent organic radical.

A bivalent organic radical in this context means to understand (d) an alkylene chain having of from 1 to 10, preferably of from 2 to 8, carbon atoms, which may be substituted by methyl or ethyl groups and which may be interrupted by ether, thioether or carboxylic acid ester groups. Examples thereof are methylene, ethylene, propylene, butylene, hexylene or octylene;

(e) a group of the formula —CH$_2$—O—A—CH$_2$—, wherein A represents a phenylene or naphthylene radical, which may be substituted by 1 or 2 alkyl groups having of from 1 to 4 carbon atoms, or by 1 or 2 halogen atoms, preferably chlorine, or an alkylene chain having of from 2 to 12, preferably of from 2 to 6, carbon atoms and being optionally substituted by methyl or ethyl groups and interrupted by ether, thioether, or carboxylic acid ester groups, or a 1,3- or 1,4-dimethylene cyclohexane radical. A may further represent an α,ω-diacylalkylene radical having of from 3 to 12, preferably of from 4 to 10, carbon atoms, which may be substituted by methyl or ethyl groups and optionally be interrupted by ether, thioether or carboxylic acid ester groups, for example, a succinic acid, a glutaric acid, an adipic acid, an azelaic acid, a sebacic acid, a diglycolic or a thiodiglycolic acid radical. A may finally represent a diacylphenylene or diacylnaphthylene radical which may be substituted by 1 or 2 alkyl groups having of from 1 to 4 carbon atoms, or by 1 to 4 halogen atoms, preferably chlorine, for example an o-, iso- or terephthalic acid radical, a tetrachloroorthophthalic acid radical, a naphthalenedicarboxylic acid radical or a chloronaphthalenedicarboxylic acid radical;

(f) a group of the formula

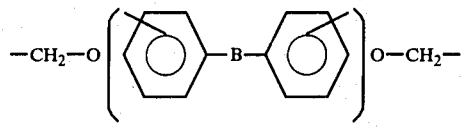

wherein B represents an oxygen or a sulfur atom, a —CO—, —SO$_2$—, or a

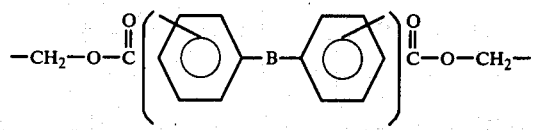

wherein D and E may be identical or different, and represent hydrogen atoms, or alkyl groups having of from 1 to 6 carbon atoms, for example methyl, ethyl, propyl, or butyl groups, or D and E may be common members of an alkylene chain having of from 4 to 6 carbon atoms, and (g) a group of the formula

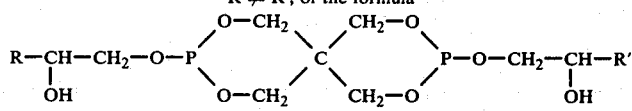

wherein B is defined as sub (f).

The novel phosphites are furthermore characterized by the fact that the total number of all carbon atoms contained in the radicals R and R', in the case of m being 2, is at least 14, preferably at least 18, and not greater than 120.

The following compounds, which are subdivided in 5 groups, show typical representatives of the phosphites according to the invention. Denotations as $C_{12/14}$-alkyl, $C_{18/22}$-alkyl, $C_{22/26}$-alkyl, and $C_{30}^\sim$-alkyl mean to say that the products have been obtained by reaction of 1,2-alkanediol mixtures.

1. group

Phosphites, wherein n = 1 and R = R' or R ≠ R', of the formula $$R-CH-CH_2-O-P \begin{matrix} O-CH_2 \\ \diagdown \\ O-CH_2 \end{matrix} C \begin{matrix} CH_2-O \\ \diagup \\ CH_2-O \end{matrix} P-O-CH_2-CH-R'$$
$$\quad\;\; | \qquad\qquad\qquad\qquad\qquad\qquad\qquad\qquad\qquad | $$
$$\quad\;\; OH \qquad\qquad\qquad\qquad\qquad\qquad\qquad\qquad OH$$

R = R' = C$_{12}$H$_{25}$-n-alkyl
R = R' = C$_{12/14}$-alkyl
R = R' = C$_{18/22}$-alkyl
R = R' = C$_{22/26}$-alkyl
R = R' = C$_{30}^\sim$-alkyl
R = R' = n-C$_{17}$H$_{35}$—CO—O—CH$_2$—
R = R' = C$_6$H$_5$—O—CH$_2$—
R = R' = n-C$_{18}$H$_{37}$—S—CH$_2$—

| R | R' |
|---|---|
| R = n-C$_8$H$_{17}$; | R' = C$_{30}^\sim$-alkyl |
| R = C$_{12/14}$-alkyl; | R' = C$_{18/22}$-alkyl |
| R = C$_{12/14}$-alkyl; | R' = C$_{22/26}$-alkyl |
| R = C$_{12/14}$-alkyl; | R' = C$_{30}^\sim$-alkyl |
| R = C$_{18/22}$-alkyl; | R' = C$_{22/26}$-alkyl |
| R = C$_{18/22}$-alkyl; | R' = C$_{30}^\sim$-alkyl |
| R = C$_{22/26}$-alkyl; | R' = C$_{30}^\sim$-alkyl |
| R = C$_{12/14}$-alkyl; | R' = n-C$_{17}$H$_{35}$—CO—O—CH$_2$— |
| R = C$_{18/22}$-alkyl; | R' = n-C$_{17}$H$_{35}$—CO—O—CH$_2$— |
| R = C$_{30}^\sim$-alkyl; | R' = n-C$_{17}$H$_{35}$—CO—O—CH$_2$— |
| R = C$_{30}^\sim$-alkyl; | R' = C$_6$H$_5$—O—CH$_2$— |

2. group

Phosphites, wherein n = 1 and R = R', of the formula

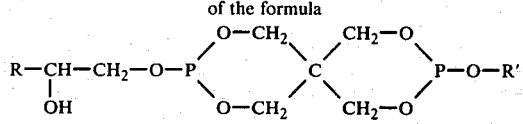

| R | R' |
|---|---|
| R = C$_{12/14}$-alkyl; | R' = C$_{18}$H$_{37}$-n-alkyl |
| R = C$_{18/22}$-alkyl; | R' = C$_{18}$H$_{37}$-n-alkyl |
| R = C$_{30}^\sim$-alkyl; | R' = C$_{18}$H$_{37}$-n-alkyl |
| R = C$_{18/22}$-alkyl; | R' = Phenyl- |
| R = C$_{30}^\sim$-alkyl; | R' = Phenyl- |
| R = C$_{30}^\sim$-alkyl; | R' = Nonylphenyl- |
| R = C$_{14}$H$_{29}$-n-alkyl; | R' = Cyclohexyl- |
| R = n-C$_{17}$H$_{35}$—CO—O—CH$_2$—; | R' = Phenyl- |
| R = n-C$_{12}$H$_{25}$—O—CH$_2$—; | R' = C$_{12}$H$_{25}$-n-alkyl |

2. group-continued

Phosphites, wherein n = 1 and R = R', of the formula

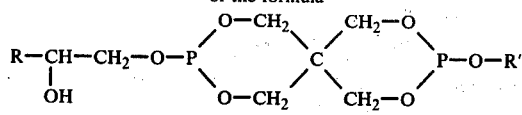

R = $C_8H_{17}$—O—$(CH_2)_2$—O—$(CH_2)_2$—O—$CH_2$—;  R' = $C_{30}H_{61}$-n-alkyl
R = $CH_3$—$(CH_2)_7$—CH=CH—$(CH_2)_7$—CO—O—$CH_2$—;  R' = $C_{16}H_{33}$-n-alkyl
R = Phenyl;  R' = $C_{18}H_{37}$-n-alkyl

3. group

Phosphites, wherein n = 2, m = 0 and R' represents identical or different radicals of the formula

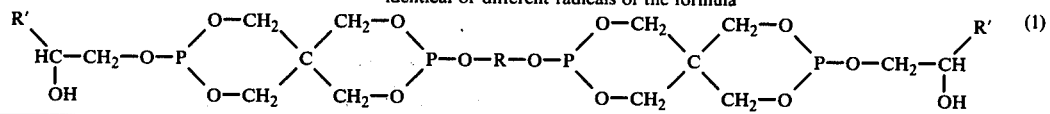 (1)

R' = R'$_{(1)}$ = $C_{12/14}$-alkyl
R' = R'$_{(1)}$ = $C_{16}H_{33}$-n-alkyl
R' = R'$_{(1)}$ = $C_{18/22}$-alkyl
R' = R'$_{(1)}$ = $C_{30}$-alkyl
R' = R'$_{(1)}$ = Phenyl
R' = R'$_{(1)}$ = n-$C_{12}H_{25}$—O—$CH_2$—
R' = R'$_{(1)}$ = n-$C_{17}H_{35}$—S—$CH_2$—

R' = $C_{12/14}$-alkyl; R'$_{(1)}$ = $C_{18/22}$-alkyl
R' = $C_{12/14}$-alkyl; R'$_{(1)}$ = $C_{30}$-alkyl
R' = $C_{18/22}$-alkyl; R'$_{(1)}$ = $C_{30}$-alkyl

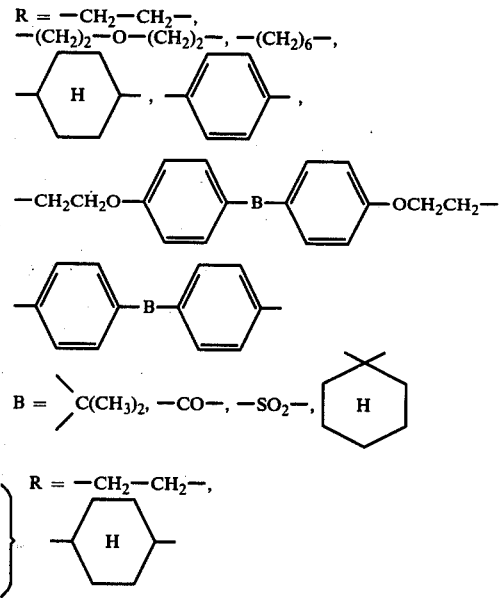

R = —$CH_2$—$CH_2$—, —$(CH_2)_2$—O—$(CH_2)_2$—, —$(CH_2)_6$—,

R = —$CH_2$—$CH_2$—,

4. group

Phosphites, wherein n = 2, m = O and r'represents identical or different radicals of the formula

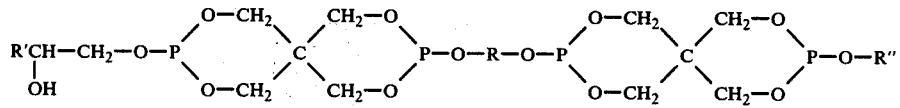

R'= R''= $C_{16}H_{33}$-n-alkyl
R'= R''= $C_{18}H_{37}$-n-alkyl

R'= $C_{12/14}$alkyl;
R''= $C_{18}H_{37}$-n-alkyl

R'= $C_{18/22}$-alkyl;
R''= $C_{18/37}$-n-alkyl

R'= $C_{30}$-alkyl;
R''= $C_{18}H_{37}$-n-alkyl
R'= n-$C_{17}H_{35}$—CO—O—$CH_2$—;
R''= $C_{18}H_{37}$-n-alkyl R'= $C_{18/22}$-alkyl;
R''= Phenyl

R = —$CH_2$—$CH_2$—,

—$(CH_2)_2$—O—$(CH_2)_2$—, —(CH''=—,

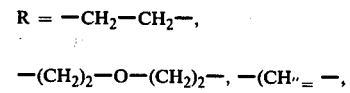

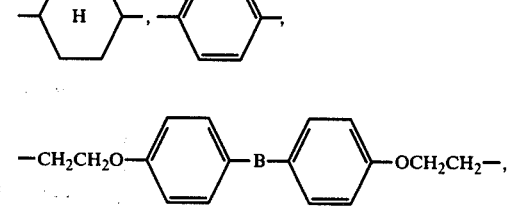

4. group-continued

Phosphites, wherein n = 2, m = O and r' represents identical or different radicals of the formula

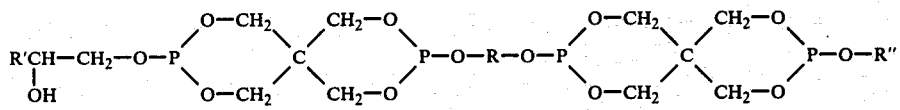

R' = C₃₀alkyl;
R" = Phenyl
R' = C₁₇H₃₅—CO—O—CH₂—;
R" = Nonylphenyl

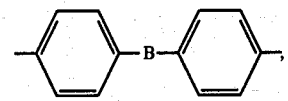

B = —C(CH₃)₃, —CO—, —SO₂—, 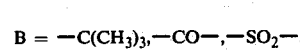

R' = C₁₂H₂₅-n-alkyl;
R" = C₃₀H₆₁-n-alkyl

5. group

Phosphites, wherein n = 2, m = 2 and R' and R" represent identical or different radicals of the formula

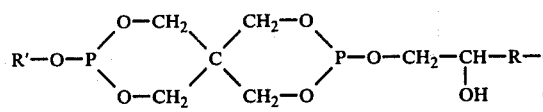 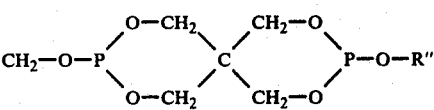

R' = R" = C₁₂H₂₅-n-alkyl

R' = R" = C₁₈H₃₇-n-alkyl

R = —(CH₂)₄—; —CH₂—O—(CH₂)₆—O—CH₂—; —CH₂—O—(CH₂)₂—S—(CH₂)₂—O—CH₂—; —CH₂—O—CH₂—CO—O—(CH₂)₂—O—CH₂—; —CH₂—O—CO—(CH₂)₄—CO—O—CH₂—;

R' = R" = C₃₀H₆₁-n-alkyl

R' = R" = n-C₁₆H₃₃—CH(OH)—CH₂—
R' = R" = n-C₂₀H₄₁—CH(OH)—CH₂—

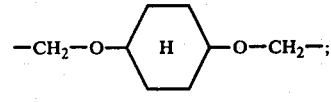

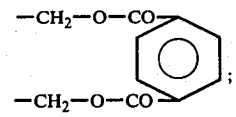

R' = n-C₁₇H₃₅—CO—O—CH₂—CH(OH)—CH₂—;
R" = Phenyl

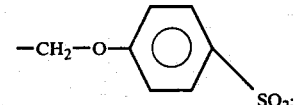

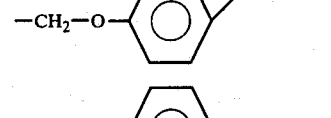

R' = n-C₁₂H₂₅—CH(OH)—CH₂—;
R" = C₁₈H₃₇-n-alkyl

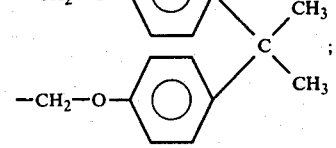

| 5. group-continued |
|---|
| Phosphites, wherein n = 2, m = 2 and R' and R" represent identical or different radicals of the formula 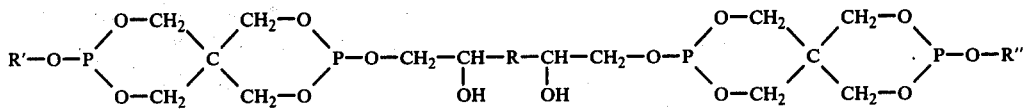 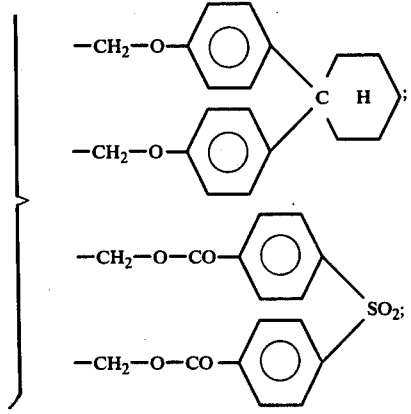 |

The phosphites according to the present invention may be used alone or in admixture with other additives selected from stabilizing known stabilizer additives, antioxidants, ultraviolet-stabilizing compounds, optionally in the presence of for example lubricants, plasticizers, pigments, fillers and auxiliaries etc. There are used from 0.01 to 10, preferably from 0.05 to 2.0, and especially from 0.1 to 1, parts by weight, calculated on 100 parts by weight of polymer.

When chlorinated polymers, such, for example as chloropolyethylene, rigid and soft polyvinyl chloride, polyvinylidene chloride, polyvinylchloroacetate and vinyl chloride copolymers, especially vinyl chloride-α-olfein-copolymers are processed, a substantially improved stability to heat and to light is achieved by adding the phosphites according to the invention in the presence of a metal compound known as a stabilizer, indoles substituted in in the 2-position, preferably 2phenylindole, epoxide stabilizers and optionally polyhydric alcohols.

Suitable metal compounds known as stabilizers are, for example, C, Ba, Sr, Zn, Cd, Mg, Al and Pb soaps of aliphatic carboxylic acids or oxycarboxylic acids having of from about 8 to 32, preferably from 8 to 24, carbon atoms, salts of these metals with aromatic carboxylic acids of preferably from 7 to 12 carbon atoms, for example benzoates, salicylates as well as (alkyl)phenolates of these metals, the alkyl radical having of from 1 to 12, preferably of from 1 to 6, carbon atoms. This range of compounds also includes organo-tin compounds, for example dialkyltin-thioglycolates and carboxylates as well as optionally neutral and basic salts of mineral acids, for example of sulfuric acid and phosphorous acid.

Known epoxide stabilizers are, for example, higher epoxidized fatty acids, such, for example, as epoxidized soybean oil, tall oil or linseed oil, epoxidized butyloleate and higher epoxyalkanes.

Polyhydric alcohols are, for example, pentaerythritol, trimethylol propane, sorbitol or manitol, i.e. preferably alcohols having of from 5 to 6 carbon atoms and from 3 to 6 OH groups.

An efficient stabilizer combination for processing halogenated polymer molding compositions consists, for example, of from 0.01 to 10 parts by weight, preferably of from 0.1 to 2 parts by weight, of a phosphite according to the invention, of from 0.1 to 10 parts by weight of a metal compound known as a stabilizer, 0.1 to 10 parts by weight of a known epoxide stabilizer and 0 to 1 part by weight of a polyhydric alcohol.

The phosphites according to the invention display also an excellent efficiency for stabilizing polymers and copolymers free from halogen. The stability of, for example, polypropylene to heat and light is considerably improved by the addition of the phosphites according to the invention, especially in admixture to phenolic and/or sulfidic stabilizers.

Suitable phenolic and sulfidic stabilizers are, for example, the generally known stabilizers against heat and light which are used in the processing of plastics, for example 3,5-ditertiarybutyl-4-hydroxyphenyl-propionic acid ester, 2,6-ditertiarybutyl-p-cresol, alkylidene-bis-alkyl-phenols, esters of bis-(4'-hydroxy-3'-tertiarybutyl-phenyl)-butyric acid, thiodipropionic acid ester of fatty alcohols as well as dioctadecyl sulfide or dioctadecyl disulfide.

A synergistically efficient stabilizer composition for polymers of olefins free from halogen consists, for example, of from 0.05 to 5 parts by weight, preferably 0.05 to 1.0 part by weight, of a phosphite according to the invention, of from 0.5 to 3 parts by weight of a known phenolic stabilizer and/or 0.1 to 3 parts by weight of a known sulfidic stabilizer.

Special stabilizers against ultra-violet rays may also be added to the stabilizer composition in an amount of from 0.1 to 3 parts by weight. Known ultra-violet absorbers are, for example, alkoxyhydroxybenzophenones, hydroxyphenylbenzotriazoles, salicilic acid phenolic esters, benzoic acid hydroxyphenolic esters, benzylidene malonic acid mononitrile esters as well as so-called "quenchers" such for example, as nickel chelates, hexamethyl-phosphoric acid triamide or, piperidine stabilizers.

Stabilizer compositions consisting of the phosphites according to the invention and of known stabilizers not only improve the stability of polyolefins, chloropolyolefins and chlorinated vinyl polymers but impart also an improved stability to polyesters, polyamides, polyacrylonitrile, polycarbonates, polysiloxanes, polyethers, polyurethanes and others.

The following examples illustrate the invention:

EXAMPLE 1

A 1 liter-four-necked flask, equipped with an agitating device, an internal thermometer, gas inlet and descending cooler, was rinsed with nitrogen and subsequently charged with 68 g (0.5 mol) of dry pentaerythritol, 166 g (1.0 mol) of freshly distilled triethyl phosphite and 0.2 g of triethylamine.

The contents of the flask were heated to 125° to 130° C. in the course of 20 to 30 minutes in a weak nitrogen current, while stirring, ethanol then starting to separate at an internal temperature of about 120° C. Within a further 2 to 3 hours, while stirring was continued, the temperature of the reaction mixture was slowly increased from 130° C. to a final temperature of from 175° to 180° C. 90.7 g of ethanol were distilled off during this period of time. Then 482 g (~1 mol) of a 1,2-alkanediol mixture having an average number of carbon atoms of 32 were added to the clear, nearly colorless melt remaining in the reaction flask. In the course of the spontaneously starting transesterification reaction 45.5 g of ethanol were distilled off within a further 3 hours at the unaltered product temperature of from 175° to 180° C.

Thus the total quantity of separated ethanol was 136.2 g (98.8% of the theoretical yield).

The slightly limpid, yellowish reaction product was allowed to settle for about 15 minutes, the clear melt was decanted from a small quantity of a bottom product. After cooling down the melt, 557 g (96.5% of the theory) of di-(2-hydroxy-$C_{32}$alkyl)-pentaerythrityl-diphosphite were obtained as a white wax having a flow-drop point of from 82° to 84.5° C. (determined according to DGF M III 3 (57)), containing 5.1% of phosphorus, and having a molecular weight of 1,210. The calculated values for a compound of formula $C_{69}H_{138}O_7P_2$ were 5.4% P and a molecular weight of 1,156.

EXAMPLE 2

According to the method described in Example 1, 68 g (0.5 mol) of pentaerythritol and 166 g (1.0 mol) of triethyl phosphite were reacted in the presence of 0.2 g of triethylamine.

Thereafter 241 g (~0.5 mol) of a 1,2-alkanediol mixture having an average number of carbon atoms of 32 as well as 164 g (~0.5 mol) of a 1,2-alkanediol mixture having of from 20 to 24 carbon atoms were added.

Upon completion of the transesterification there were obtained 482 g (96.4% of the theory) of a white, wax-like phosphite having a flow-drop point of from 69° to 81.5° C. Phosphorus content: 6.1%, molecular weight 980. Theory: 6.2% P, molecular weight 1,002.

EXAMPLE 3

According to the method described by Example 1, 68 g (0.5 mol) of pentaerythritol and 166 g (1.0 mol) of triethyl phosphite were reacted in the presence of 0.2 g of triethylamine.

Thereafter 241 g (~0.5 mol) of a 1,2-alkanediol mixture having an average number of carbon atoms of 32 and 122 g (~0.5 mol) of a 1,2-alkanediol mixture having of from 14 to 16 carbon atoms, were added.

There was obtained 450 g (98% of the theory) of a yellowish, wax-like phosphite having a flow-drop point of from 78° to 81° C. Phosphorus content: 6.6%. Theory: 6.8% P, molecular weight 918.

EXAMPLE 4

The reaction product obtained according to the method described by Example 1 from 68 g (0.5 mol) of pentaerythritol and 166 g (1.0 mol) of triethyl phosphite in the presence of 0.2 g of triethylamine, was reacted with 328 g (~1 mol) of a 1,2-alkanediol mixture having of from 20 to 24 carbon atoms.

There were obtained 413 g (97.4% of the theory) of a pure white, wax-like phosphite having a flow-drop point of from 63° to 64° C. Phosphorus content 7.0%, molecular weight 807. Theory: 7.3% P and molecular weight 848.

EXAMPLE 5

According to the method described by Example 1, 68 g (0.5 mol) of pentaerythritol and 166 g (1.0 mol) of triethyl phosphite were reacted in the presence of 0.2 g of triethylamine.

Thereafter 164 g (~0.5 mol) of a 1,2-alkanediol mixture having of from 20 to 24 carbon atoms and 122 g of (about 0.5 mol) of an alkanediol mixture having of from 14 to 16 carbon atoms were added.

Upon completion of the transesterification reaction there were obtained 367 g (96% of the theory) of a yellowish, wax-like phosphite having a flow-drop point of from 49° to 51° C. Phosphorus content 7.7%, molecular weight 780. Theory: 8.1% P, molecular weight 764.

EXAMPLE 6

The reaction product obtained according to the method described by Example 1 from 68 g (0.5 mol) of pentaerythritol and 166 g (1.0 mol) of triethyl phosphite in the presence of 0.2 g of triethylamine was reacted with 244 g (about 1 mol) of a 1,2-alkanediol mixture having of from 14 to 16 carbon atoms.

There were obtained 330 g (97% of the theory) of a yellowish, soft wax-like phosphite having a flow-drop point of from 46° to 48° C. Phosphorus content: 9.1%, molecular weight 652. Theory: 9.1% of P, molecular weight 680.

EXAMPLE 7

According to the method described in Example 1, 68 g (0.5 mol) of pentaerythritol and 166 g (1.0 mol) of triethyl phosphite were reacted in the presence of 0.2 g of triethylamine.

Thereafter 164 g (about 0.5 mol) of a 1,2-alkanediol mixture having of from 20 to 24 carbon atoms and 179 g (0.5 mol) of glycerine monostearate were added.

Upon completion of the transesterification reaction there were obtained 420 g (95.6% of the theory) of a white, wax-like phosphite having a flow-drop point of from 52.5° to 53.5° C. Phosphorus content 6.8%, molecular weight 874. Theory: 7.1% of P, molecular weight 878.

EXAMPLE 8

The reaction product obtained according to the method described by Example 1 from 68 g (0.5 mol) of pentaerythritol and 166 g (1.0 mol) of triethyl phosphite in the presence of 0.2 g of triethylamine, was reacted with a mixture consisting of 164 g (about 0.5 mol) of a 1,2-alkanediol mixture having of from 20 to 24 carbon atoms and 135 g (0.5 mol) of stearyl alcohol.

There were obtained 375 g (95% of the theory) of a pure white, soft wax-like phosphite having a flow-drop point of from 45° to 47° C. Phosphorus content: 7.7%, molecular weight 740. Theory: 7.8% of P, molecular weight 790.

EXAMPLE 9

According to Example 1, 68 g (0.5 mol) of pentaerythritol and 166 g (1.0 mol) of triethyl phosphite were reacted in the presence of 0.2 g of triethylamine.

Thereafter 241 g (about 0.5 mol) of a 1,2-alkanediol mixture having an average number of carbon atoms of 32 and 135 g (0.5 mol) of stearyl alochol were added.

Upon completion of the transesterification reaction there were obtained 456 g (96.5% of the theory) of a white, wax-like phosphite having a flow-drop point of from 77° to 80° C. Phosphorus content:6.2%, molecular weight 922. Theory: 6.6% of P, molecular weight 944.

EXAMPLE 10

According to Example 1, there were reacted 68 g (0.5 mol) of pentaerythritol and 166 g (1.0 mol) of triethyl phosphite in the presence of 0.2 g of triethylamine.

Thereafter 168 g (1.0 mol) of 3-phenoxypropanediol-1,2 were added.

There were obtained 260 g (98% of the theory) of a colorless, viscous phosphite which had a phosphorus content of 10.8% and a molecular weight of 540. Theory: 11.7 of P, molecular weight 528.

EXAMPLE 11

According to Example 1, there were reacted 68 g (0.5 mol) of pentaerythritol and 166 g (1.0 mol) of triethyl phosphite in the presence of 0.2 g of triethylamine.

Thereafter a mixture consisting of 241 g (about 0.5 mol) of a 1,2-alkanediol mixture having an average number of carbon atoms of 32 and 15.5 g (0.25 mol) of ethylene glycol was added.

Upon completion of the transesterification reaction there were obtained 331 g (94% of the theory) of a white, wax-like phosphite having a flow-drop point of from 79.5° to 82° C. Phosphorus content: 8.5%, molecular weight 335. Theory: 8.8%, molecular weight 1,410.

EXAMPLE 12

According to Example 1, 68 g (0.5 mol) of pentaerythritol and 166 g (1.0 mol) of triethyl phosphite were reacted in the presence of 0.2 g of triethylamine.

Thereafter a mixture consisting of 241 g (about 0.5 mol) of a 1,2-alkanediol mixture having an average number of carbon atoms of 32 and 36 g (0.25 mol) of 1,4-dimethylolcyclohexane was added.

Upon completion of the transesterification reaction there were obtained 358 g (96% of the theory) of a white, wax-like phosphite having a flow-drop point of from 81.5° to 85° C. Phosphorus content: 8.2%, molecular weight 1,400. Theory: 8.3%, of P, molecular weight 1,492.

EXAMPLE 13

According to Example 1 there were reacted 68 g (0.5 mol) of pentaerythritol and 166 g (1.0 mol) of triethyl phosphite in the presence of 0.2 g of triethylamine.

Thereafter a mixture consisting of 164 g (about 0.5 mol) of a 1,2-alkanediol mixture having of from 20 to 24 carbon atoms and 79 g (0.25 mol) of -dimethyl-bis-(4,4'-β-hydroxyethoxyphenyl) methane was added.

Upon completion of the transesterification reaction there were obtained 325 g (96% of the theory) of a white, soft wax-like phosphite having a flow-drop point of from 53.5° to 55° C. Phosphorus content: 8.6%, molecular weight 1,448. Theory: 9.1%, molecular weight 1,356.

EXAMPLE 14

According to Example 1 there were reacted 68 g (0.5 mol) of pentaerythritol and 166 g (1.0 mol) of triethyl phosphite in the presence of 0.2 g of triethylamine.

Thereafter a mixture consisting of 107 g (0.5 mol) of tetradecyl alcohol and 94 g (0.25 mol) of -dimethyl-bis-(4,4'β,γ-dihydroxy-propoxyphenyl)-methane was added.

There were obtained 291 g (98% of the theory) of a yellowish, soft wax-like phosphite having a flow-drop point of from 47.5° to 51° C. Phosphorus content: 9.8%, molecular weight 1,120. Theory: 10.4% of P, molecular weight 1,188.

EXAMPLE 15

The resistance to hydrolysis of the phosphites according to the invention in comparison with that of four trade products was determined in the following manner:

5 g of phosphite were heated to the boil in 100 ml of distilled water; after a boiling time of 20 to 60 minutes the reaction mixture was cooled and the content of phosphorus acid in the aqueous solution was determined by titration with aqueous 0.1 N sodium hydroxide solution. The degree of hydrolysis of the examined phosphite was defined arbitrarily as the ratio 100 x/y, x being the actually consumed volume of the 0.1 N NaOH and y the theoretical volume of this reagent. It was calculated presuming a complete hydrolysis of the phosphite to phosphorus acid.

| Phosphite | Degree of hydrolysis in % after a boiling time of | |
|---|---|---|
| | 20 minutes | 60 minutes |
| a) Triphenylphosphite[1] | 84 | 100 |
| b) Tris(nonylphenyl)phosphite[1] | 57 | 92 |
| c) Diphenyl-isooctylphosphite[1] | 55 | 77 |
| d) Distearyl-pentaerythrityl-diphosphite[1] | 52 | 68 |
| Phosphite according to Example | | |
| e) 1 | 6,5 | 12,4 |
| f) 2 | 13,8 | 19,5 |
| g) 3 | 46 | 58,7 |
| h) 4 | 44 | 56,3 |
| i) 5 | 54 | 60,6 |
| j) 6 | 62,2 | 68,4 |
| k) 7 | 44 | 54,2 |
| l) 8 | 48,1 | 54,9 |
| m) 9 | 22,8 | 34,8 |
| n) 10 | 81,2 | 88,6 |
| o) 11 | 17,4 | 25,5 |
| p) 12 | 16,2 | 27,8 |
| q) 13 | 39,2 | 51,6 |
| r) 14 | 51,7 | 59,3 |

[1]trade products, in comparison

EXAMPLES 16 TO 51

These Examples illustrate the stabilizing effect of phosphites according to the invention on the processing of polyvinyl chloride. The dynamic stability under heat (Examples 16 to 33) and the static stability under heat (Examples 34 to 51) were determined. The specified parts are parts by weight.

For each of a number of phosphites 100 parts of a mass-polyvinylchloride having a K-value of 60 were mixed thoroughly with 0.2 parts of 2-phenylindole, 3 parts of epoxidized soybean oil, 0.25 parts of a complex calcium/zinc stabilizer consisting of 42% by weight of calcium stearate, 30% by weight of zinc stearate, 22% by weight of pentaerythritol and 6% by weight of 2,6-di-t-butyl-4-methyl-phenol, 0.2 part of a montanic acid ester (acid number 18, saponification number 154), 0.3 part of stearyl stearyte, 0.5 part of glycerolmono-stearate, and 0.5 part by weight of the phosphite.

In order to determine the dynamic stability under heat each mixture was applied on to a laboratory-scale twin-roller device heated to 180° C., and rolled-out to a sheet within one minute at 20 rpm. At intervals of 10 minutes, samples were picked of these sheets, and their color shades compared with an internal color chart. The various tests were run until the rolled-out sheet had taken up a dark-brown to black shade.

the roller and sheets of about 0.5 mm thickness and a diameter of 30 mm blanked therefrom. The sheets were wrapped in aluminum sheet and tempered at 180° C. in a heating cabinet with internal air circulation. One sheet was selected every 10 minutes and its color shade compared with the color chart. The figures employed in the color chart have the following meaning:

1 = clear as water
2 = slightly yellowish
3 = distinctly yellow tint
4 = dark yellow-brown shade
5 = dark brown to black As demonstrated by the following tables, as far as dynamic stability under heat and static stability under heat are concerned, the polyvinyl chloride stabilized by organic phosphites of the present invention is clearly superior in comparison to polyvinyl chloride stabilized with known phosphites and with mixtures free from phosphites.

| Example No. | Phosphite acc. to Example | Discoloration of the rough sheet at a rolling tim of | | | | | | | |
|---|---|---|---|---|---|---|---|---|---|
| | | 10' | 20' | 30' | 40' | 50' | 60' | 70' | 80' |
| | | compared with color chart | | | | | | | |
| 16 | 1 | 1 | 1 | 2 | 2 | 3 | 3–4 | 4 | 5 |
| 17 | 2 | 1 | 1–2 | 2 | 2–3 | 3 | 3–4 | 4–5 | 5 |
| 18 | 3 | 1 | 2 | 2 | 2–3 | 3 | 3–4 | 5 | |
| 19 | 4 | 1 | 1–2 | 2 | 2–3 | 3 | 3–4 | 5 | |
| 20 | 5 | 1–2 | 2 | 2–3 | 3 | 3–4 | 3–4 | 5 | |
| 21 | 6 | 2 | 2–3 | 2–3 | 3 | 3 | 3–4 | 4 | 5 |
| 22 | 7 | 1–2 | 2 | 2–3 | 3 | 3–4 | 4 | 4–5 | 5 |
| 23 | 8 | 1–2 | 2 | 2 | 2–3 | 3 | 3–4 | 4 | 5 |
| 24 | 9 | 1 | 1–2 | 2 | 2–3 | 3 | 3–3 | 4 | 5 |
| 25 | 10 | 2 | 2–3 | 2–3 | 3 | 3–4 | 4 | 5 | |
| 26 | 11 | 1 | 1–2 | 2 | 2–3 | 3 | 3–4 | 4–5 | 5 |
| 27 | 12 | 1 | 1 | 2 | 2 | 3 | 3–4 | 4 | 5 |
| 28 | 13 | 1 | 1–2 | 2 | 2–3 | 3 | 3–4 | 5 | |
| 29 | 14 | 2 | 2–3 | 2–3 | 3 | 3 | 3–4 | 4 | 5 |
| 30 (comp.) | 15 a) | 1 | 2 | 2–3 | 5 | | | | |
| 31 (comp.) | 15 c) | 1 | 2 | 3 | 5 | | | | |
| 32 (comp.) | 15 d) | 2 | 2–3 | 3 | 3 | 3–4 | 4–5 | 5 | |
| 33 (comp.) | without | 2 | 2–3 | 3–4 | 5 | | | | |

| Static stability under heat | | | | | | | | | | |
|---|---|---|---|---|---|---|---|---|---|---|
| Example No. | Phosphite acc. to Example, | Discoloration of the sheet in the heating cabinet at a tempering period of | | | | | | | | |
| | | 0' | 20' | 30' | 40' | 50' | 60' | 70' | 80' | 100' |
| | | compared with color chart | | | | | | | | |
| 34 | 1 | 1 | 2 | 2 | 3 | 3 | 3–4 | 4 | 5 | |
| 35 | 2 | 1 | 1–2 | 2 | 2–3 | 3 | 3 | 4 | 5 | |
| 36 | 3 | 1 | 2 | 2– | 3 | 3 | 4 | 4–5 | 5 | |
| 37 | 4 | 1 | 2 | 2–3 | 3 | 3 | 3 | 4 | 4–5 | 5 |
| 38 | 5 | 1–2 | 2 | 2 | 2–3 | 3 | 3 | 3 | 3–4 | 5 |
| 39 | 6 | 2 | 3 | 3 | 3 | 3–4 | 3–4 | 4–5 | 5 | |
| 40 | 7 | 1–2 | 2 | 2–3 | 2–3 | 3 | 3–4 | 3–4 | 5 | |
| 41 | 8 | 1–2 | 2 | 2–3 | 2–3 | 3 | 4 | 5 | | |
| 42 | 9 | 1 | 2 | 2 | 2–3 | 3 | 3–4 | 3–4 | 5 | |
| 43 | 10 | 2 | 2–3 | 2–3 | 3 | 3–4 | 4 | 5 | | |
| 44 | 11 | 1 | 1–2 | 2 | 2–3 | 3 | 3 | 4 | 5 | |
| 45 | 12 | 1 | 2 | 2 | 3 | 3 | 3–4 | 4 | 5 | |
| 46 | 13 | 1 | 2 | 2–3 | 3 | 3 | 3 | 4 | 4–5 | 5 |
| 47 | 14 | 2 | 3 | 3 | 3 | 3–4 | 3–4 | 4–5 | 5 | |
| 48 (comp.) | 15 a) | 1 | 1–2 | 2 | 2–3 | 3 | 5 | | | |
| 49 (comp.) | 15 c) | 1 | 2 | 2 | 2 | 3 | 3–4 | 5 | | |
| 50 (comp.) | 15 d) | 2 | 2–3 | 2–3 | 3 | 3–4 | 3–4 | 4 | 5 | |
| 51 (comp.) | without | 1 | 2 | 2–3 | 3 | 3–4 | 3–4 | 5 | | |

In order to determine the static stability under heat, a rolled-out sheet was first prepared from each mixture according to the description given above, and this sheet was rolled-out on the twin-roller device for another 10 minutes' period at 180° C. The sheet was then peeled off

EXAMPLES 52 TO 55

These Examples show that the addition of the phosphites according to the invention to polypropylene improves considerably its stability to light and against alteration due to heat.

A powdery mixture consisting of
100 parts by weight of unstabilized polypropylene (i₅ (230° C.) about 8),
0.15 part by weight of octadecyl-3-(3',5'-di-tert.-butyl-4'-hydroxyphenyl)-propionate and
0.10 part by weight of the phosphites prepared according to Examples 1, 2 and 9 was injection-molded on an injection molding machine to yield test plates measuring 60 x 60 y 1 mm. Test specimens were blanked from these plates.

The stability to light was determined by means of the Xenotest device, type 150, produced by Messrs. Hanau Quarzlampen GmbH with the filter combination 6 IR + 1 UV as per DIN 53 387 (DIN = German Industrial Standard). The time of exposure to light, i.e. the period of time after which the absolute elongation at break had decreased to 10%, was measured.

The resistance to alteration under heat (weathering resistance) of injection molded test samples was measured approximately to the procedure described by DIN 53 383 at an air temperature of 140° C. It was used on the one hand to determine the time of exposure to light of the test specimens and to evaluate the phosphites according to the invention.

The following table shows the good stability to light and the heat-stabilizing effect of the phosphites according to the invention used in polypropylene.

| Example No. | Phosphite acc. to Example | Time of exposure to light in hours | Weathering resistance under heat in days |
|---|---|---|---|
| 52 | 1 | 975 | 57 |
| 53 | 2 | 810 | 48 |
| 54 | 9 | 945 | 55 |
| 55 (comp.) | without | 540 | 22 |

We claim:
1. A phosphite of the formula

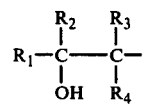

in which n is 1 or 2 and wherein, in the case of n being 1,
R and R' are identical or different and at least one of R and R' represents a group of the formula $$R_1-\underset{\underset{OH}{|}}{\overset{\overset{R_2}{|}}{C}}-\underset{\underset{R_4}{|}}{\overset{\overset{R_3}{|}}{C}}-$$

wherein the radicals $R_1$ to $R_4$ stand for identical or different radicals, which may be
(a) 0 to 3 hydrogen atoms,
(b) a straight chain or branched alkyl radical having of from 1 to 60 carbon atoms, the sum of all carbon atoms contained in the radicals $R_1$ to $R_4$ being at least 4 and not greater than 60, whereas the optionally remaining radical R or R' may be
(c) a straight chain or branched alkyl radical having of from 1 to 60 carbon atoms, the sum of all carbon atoms contained in the radicals R and R' being at least 10, and not greater than 120, and in the case of n being 2, R and R' are different, R' in both parts of the molecule linked by R is equal or different and is defined as in the case of n being 1, and R represents a bivalent organic radical, which may be
(d) an alkylene chain having of from 2 to 16 carbon atoms,
(e) a 1,3- or 1,4-dimethylene cyclohexane radical,
(f) a group of the formula

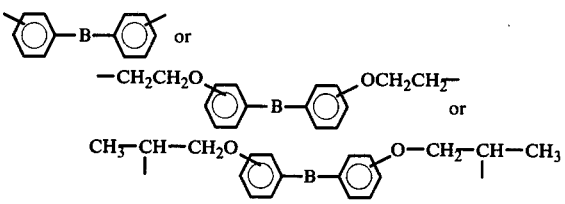

wherein B is —O—, —S—, —CO—, —SO₂— or

D and E being equal or different and each represent a hydrogen atom, or an alkyl radical having of from 1 to 6 carbon atoms or D and E may be common members of an alkylene chain having of from 4 to 6 carbon atoms and the sum of all carbon atoms contained in the radicals R and R' is at least 12 and not greater than 120.

2. Phosphite as claimed in claim 1, wherein the radicals specified sub (b) contain further ether, thioether or carboxylic acid ester groups.

3. Phosphite as claimed in claim 1, wherein the radicals specified sub (c) contain further ether, thioether or carboxylic acid ester groups.

4. Phosphite as claimed in claim 1, wherein the alkylene chain specified sub (d) is substituted by methyl or ethyl groups and optionally interrupted by ether, thioether or carboxylic acid ester groups.

5. Phosphite as claimed in claim 1, wherein n is 1, R and R' are identical or different and $R_1$ is a straight chain or branched alkyl group having of from 10 to 58 carbon atoms, $R_3$ and $R_4$ are hydrogen atoms, $R_2$ is a hydrogen atom or a methyl or an ethyl group and the sum of all carbon atoms contained in the radicals $R_1$ to $R_4$ is in the range of from 10 to 60.

6. Phosphite as claimed in claim 1, wherein n is 1, R and R' are identical or different and $R_1$ is a straight chain or branched alkyl group having of from 10 to 58 carbon atoms, $R_3$ and $R_4$ are hydrogen atoms, $R_2$ is a hydrogen atom or a methyl or an ethyl group and the sum of all carbon atoms contained in the radicals $R_1$ to $R_4$ is in the range of from 10 to 60.

7. Plastic molding compositions containing as stabilizer a phosphite as claimed in claim 1.

* * * * *